(12) United States Patent
Skakoon

(10) Patent No.: US 7,018,384 B2
(45) Date of Patent: Mar. 28, 2006

(54) MEDICAL PASSING DEVICE AND METHOD

(75) Inventor: James Grant Skakoon, St Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 600 days.

(21) Appl. No.: 10/230,531

(22) Filed: Aug. 29, 2002

(65) Prior Publication Data

US 2004/0044348 A1    Mar. 4, 2004

(51) Int. Cl.
*A61F 11/00*    (2006.01)
(52) U.S. Cl. ............. 606/108; 604/164.01; 604/164.06
(58) Field of Classification Search ................ 600/434; 604/158, 161, 163, 164.01, 164.06, 170.01, 604/170.02, 171; 606/108, 129, 145, 190
See application file for complete search history.

(56) References Cited

U.S. PATENT DOCUMENTS

| | | |
|---|---|---|
| 480,478 A | 9/1892 | Smith, et al. |
| 3,861,393 A | 1/1975 | Durand |
| 4,010,757 A | 3/1977 | Jula et al. |
| 4,280,510 A | 7/1981 | O'Neill |
| 4,299,228 A | 11/1981 | Peters |
| 4,327,722 A | 5/1982 | Groshong et al. |
| 4,424,818 A | 1/1984 | Doring et al. |
| 4,431,426 A | 2/1984 | Groshong et al. |
| 4,432,752 A | 2/1984 | Marlon |
| 4,453,928 A | 6/1984 | Steiger |
| 4,574,806 A | 3/1986 | McCarthy |
| 4,699,612 A | 10/1987 | Hamacher |
| 4,832,687 A | 5/1989 | Smith |
| 4,898,575 A | 2/1990 | Fischell et al. |
| 4,976,684 A | 12/1990 | Broadnax, Jr. |
| 5,036,854 A | 8/1991 | Schollmeyer et al. |
| 5,154,725 A | 10/1992 | Leopold |
| 5,163,912 A | 11/1992 | Gay et al. |
| 5,170,787 A | 12/1992 | Lindegren |

(Continued)

FOREIGN PATENT DOCUMENTS

DE    10020395    2/2001

(Continued)

OTHER PUBLICATIONS

MEDTRONIC, Model 3464 Receiver/Extension Internalization Manual, SE-4 for Spinal Cord Stimulation (SCS), 1978, Cover Page and Cols. 1-11.

(Continued)

*Primary Examiner*—Anhtuan T. Nguyen
*Assistant Examiner*—Robert Lynch
(74) *Attorney, Agent, or Firm*—Banner & Witcoff, Ltd.

(57) ABSTRACT

A medical device and method for placing a medical tube, such as a catheter or a shunt, or a medical electrical lead within a patient is disclosed. The medical device of the present invention comprises a passer having a proximal end and a distal end, the passer defining a channel between the proximal end and the distal end. The medical device of the present invention further comprises an obturator having an elongated body, and a first end and a second end, the second end comprising a cradle. In accordance with the invention, the obturator has a removable probe having a first section that fits within the cradle and a second section having a tunneling tip that is exposed outside of the cradle. The obturator is placed into the passer so that the tunneling tip of the probe is exposed outside of the passer at the distal end of the passer. The cradle has dimensions to receive and hold in place a portion of the medical tube or medical lead after the probe is removed from the cradle.

42 Claims, 10 Drawing Sheets

U.S. PATENT DOCUMENTS

| | | |
|---|---|---|
| 5,171,226 A | 12/1992 | McCrory |
| 5,190,529 A | 3/1993 | McCrory et al. |
| 5,234,438 A | 8/1993 | Semrad |
| 5,241,957 A | 9/1993 | Camps et al. |
| 5,246,014 A | 9/1993 | Williams et al. |
| RE34,466 E | 12/1993 | Newcomb et al. |
| 5,267,982 A | 12/1993 | Sylvanowicz |
| 5,275,611 A | 1/1994 | Behl |
| 5,281,236 A | 1/1994 | Bagnato et al. |
| 5,300,106 A | 4/1994 | Dahl et al. |
| 5,306,240 A | 4/1994 | Berry |
| 5,348,537 A | 9/1994 | Wiesner et al. |
| 5,417,208 A | 5/1995 | Winkler |
| 5,443,493 A | 8/1995 | Byers et al. |
| 5,571,161 A | 11/1996 | Starksen |
| 5,607,443 A | 3/1997 | Kieturakis et al. |
| 5,667,514 A | 9/1997 | Heller |
| 5,672,158 A | 9/1997 | Okada et al. |
| 5,722,425 A | 3/1998 | Bostrom |
| 5,728,148 A | 3/1998 | Bostrom et al. |
| 5,752,937 A | 5/1998 | Otten et al. |
| 5,782,841 A | 7/1998 | Ritz et al. |
| 5,871,528 A | 2/1999 | Camps et al. |
| 5,885,217 A | 3/1999 | Gisselberg et al. |
| 6,004,326 A | 12/1999 | Castro et al. |
| 6,078,841 A | 6/2000 | Kuzma |
| 6,149,657 A | 11/2000 | Kuzma |
| 6,254,610 B1 | 7/2001 | Darvish et al. |
| 6,304,785 B1 | 10/2001 | McCreery et al. |
| 6,324,414 B1 | 11/2001 | Gibbons et al. |
| 6,436,068 B1 | 8/2002 | Bardy |
| 6,475,244 B1 | 11/2002 | Herweck |
| 6,516,226 B1 | 2/2003 | Bishay et al. |
| 6,522,927 B1 | 2/2003 | Bishay et al. |
| 6,529,776 B1 | 3/2003 | Leonard et al. |
| 6,539,264 B1 | 3/2003 | Bishay et al. |
| 6,542,780 B1 | 4/2003 | Leonard |
| 6,549,810 B1 | 4/2003 | Leonard et al. |
| 6,551,314 B1 | 4/2003 | Hill et al. |
| 6,556,869 B1 | 4/2003 | Leonard et al. |
| 6,560,491 B1 | 5/2003 | Leonard et al. |
| 6,565,594 B1 | 5/2003 | Herweck et al. |
| 6,592,553 B1 | 7/2003 | Zhang et al. |
| 6,605,094 B1 | 8/2003 | Mann et al. |
| 6,613,069 B1 | 9/2003 | Boyd et al. |
| 6,622,051 B1 | 9/2003 | Bishay et al. |
| 6,752,827 B1 | 6/2004 | Ross et al. |
| 2001/0032023 A1 | 10/2001 | Herweck et al. |
| 2002/0029994 A1 | 3/2002 | Schon |
| 2003/0225426 A1 | 12/2003 | Hill et al. |
| 2004/0044348 A1 | 3/2004 | Skakoon |
| 2004/0059348 A1 | 3/2004 | Geske, et al. |
| 2004/0127889 A1 | 7/2004 | Zhang, et al. |

FOREIGN PATENT DOCUMENTS

| | | |
|---|---|---|
| EP | 0024963 | 3/1981 |
| EP | 0 494 806 | 7/1992 |
| EP | 0517494 | 12/1992 |
| EP | 0646389 | 4/1995 |
| EP | 1015063 | 4/1999 |
| EP | 1053762 | 11/2000 |
| WO | WO 97/20530 | 6/1997 |
| WO | WO 00/02623 | 1/2000 |

OTHER PUBLICATIONS

Medtronic Extension Passer 3555 Accessory Kit, Technical Instructions; (2 pages).

Medtronic Tunneling Rod Accessory Kit 8590-41, Technical Manual (9 pages).

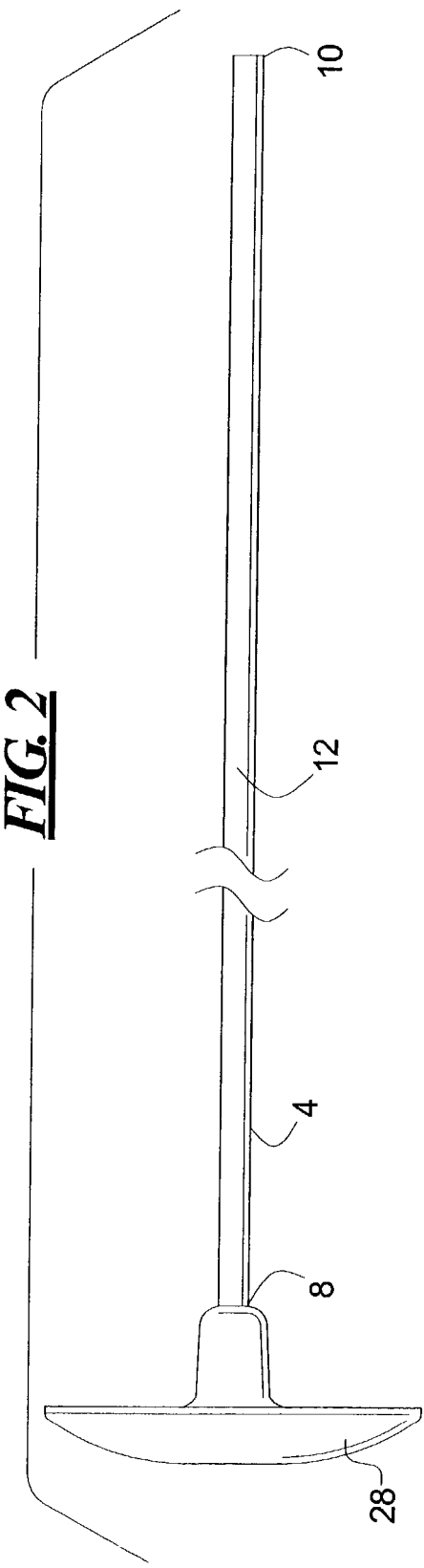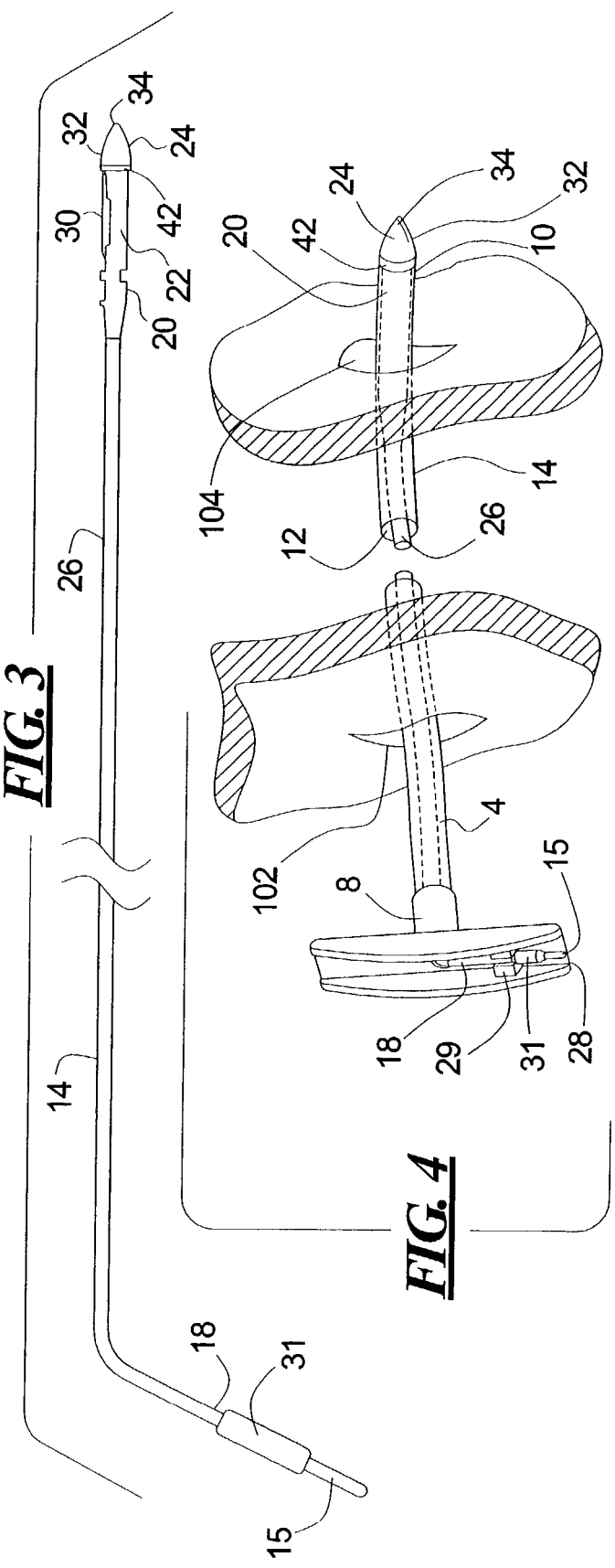

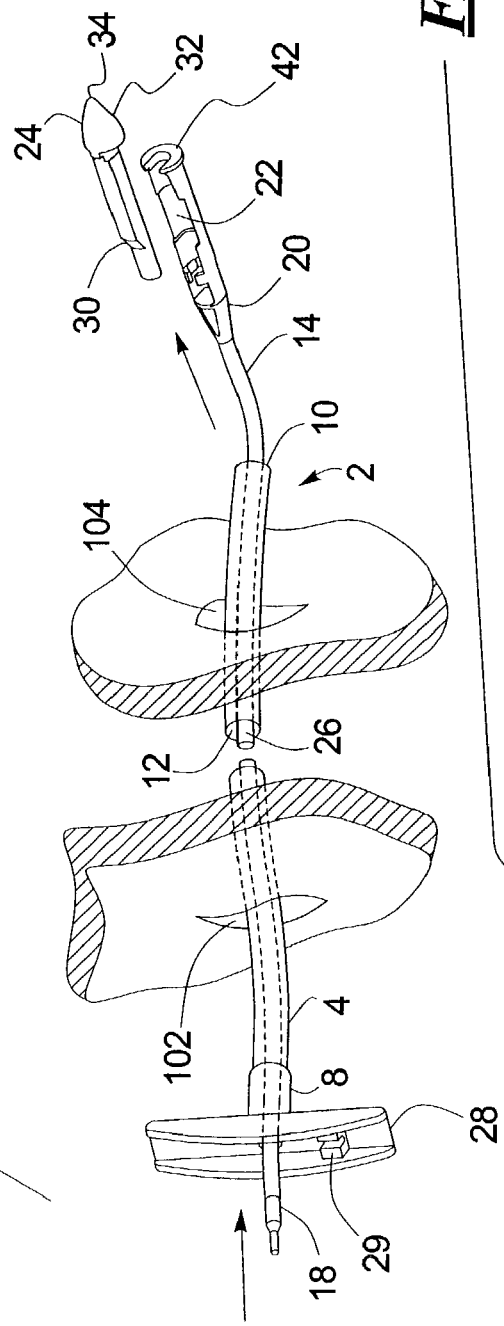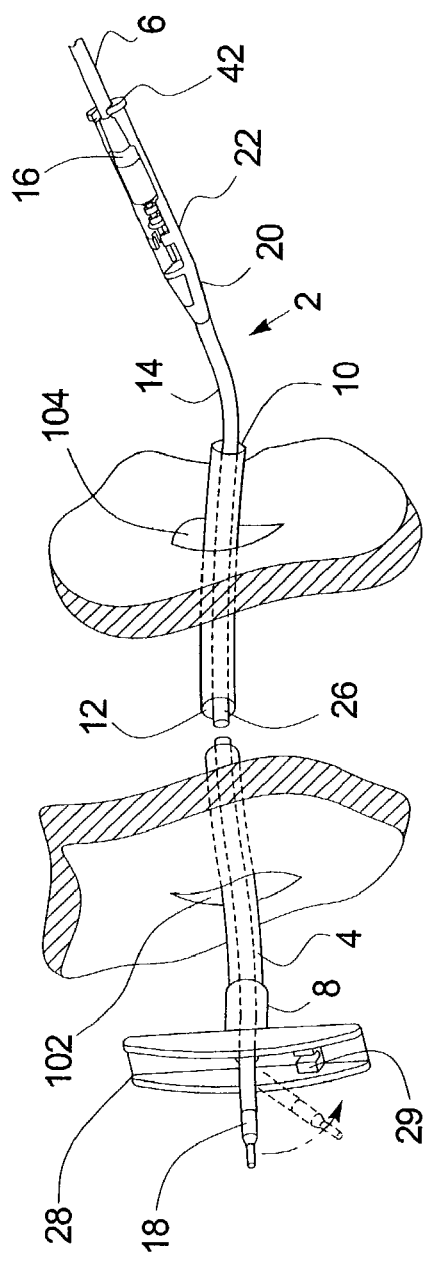

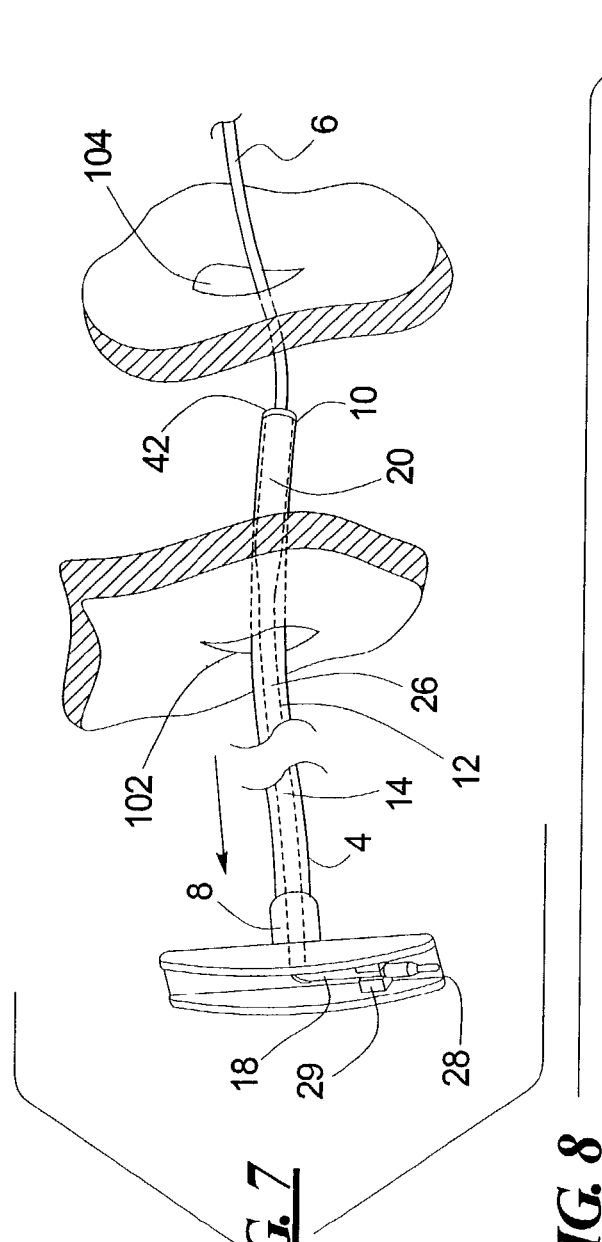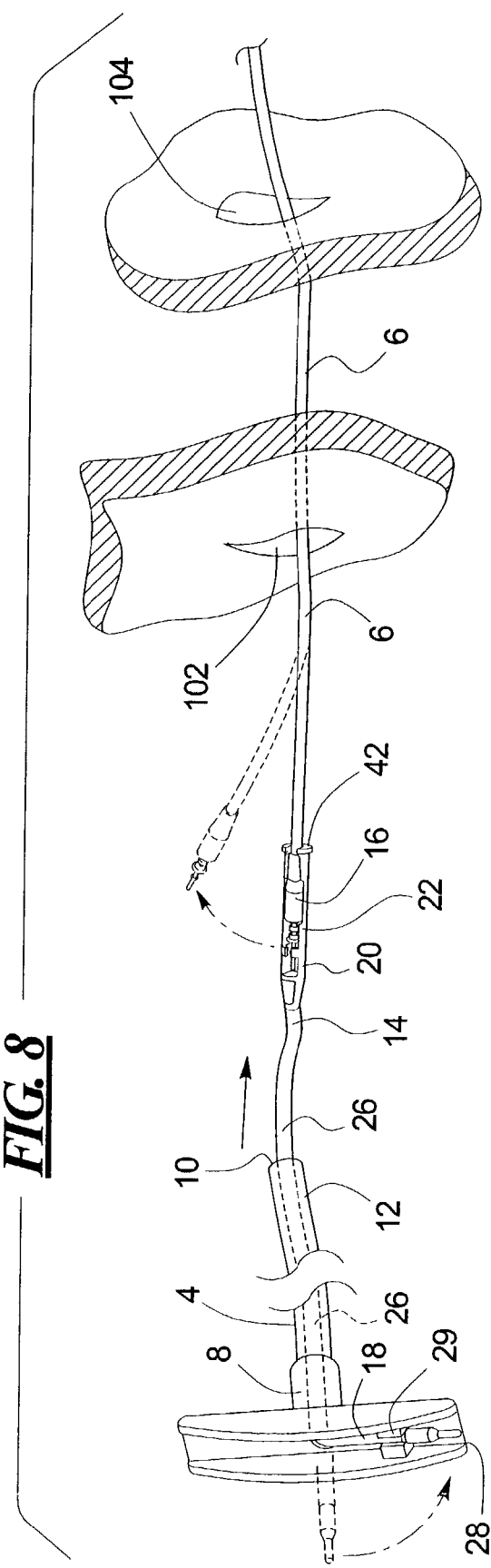

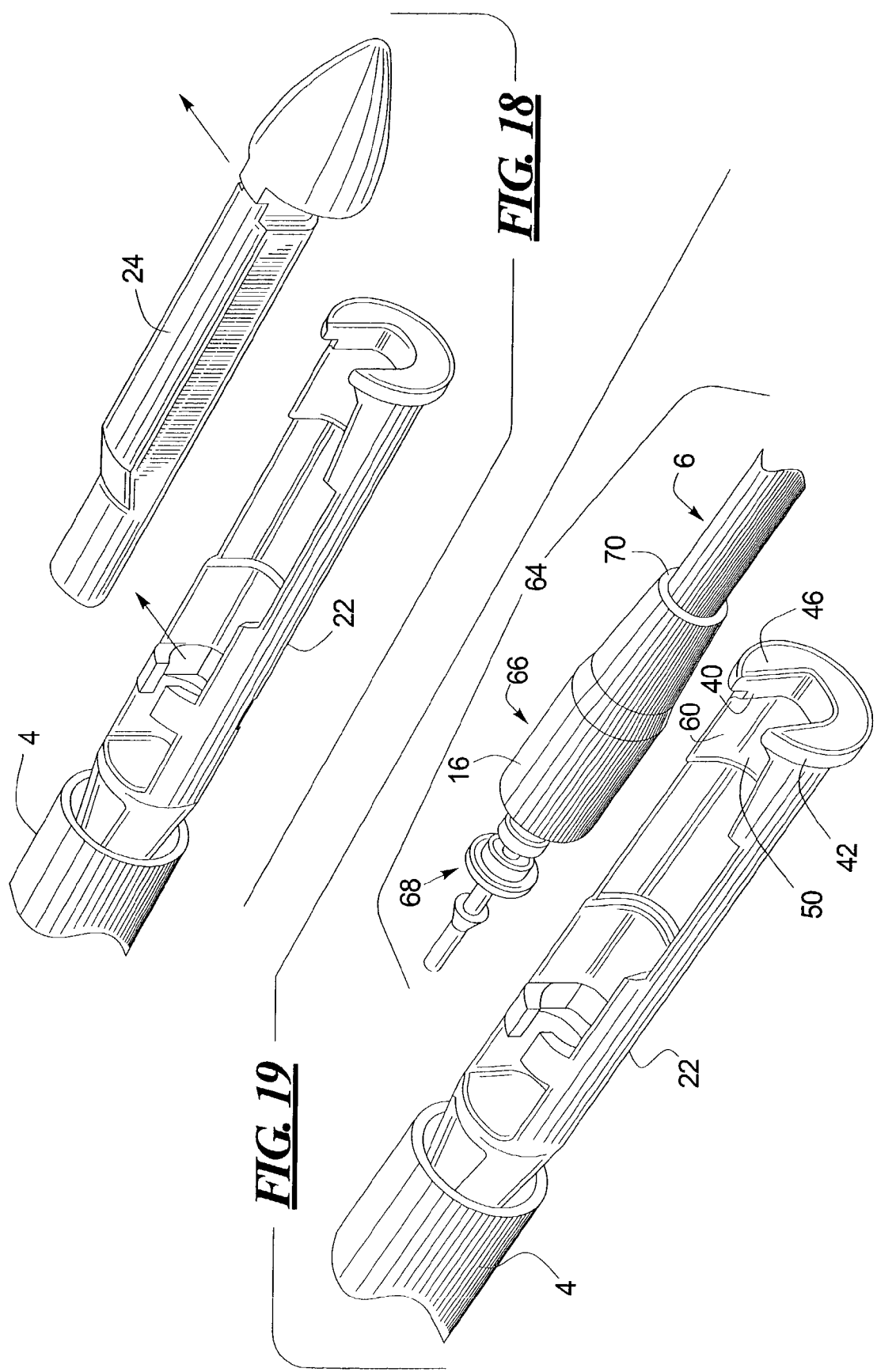

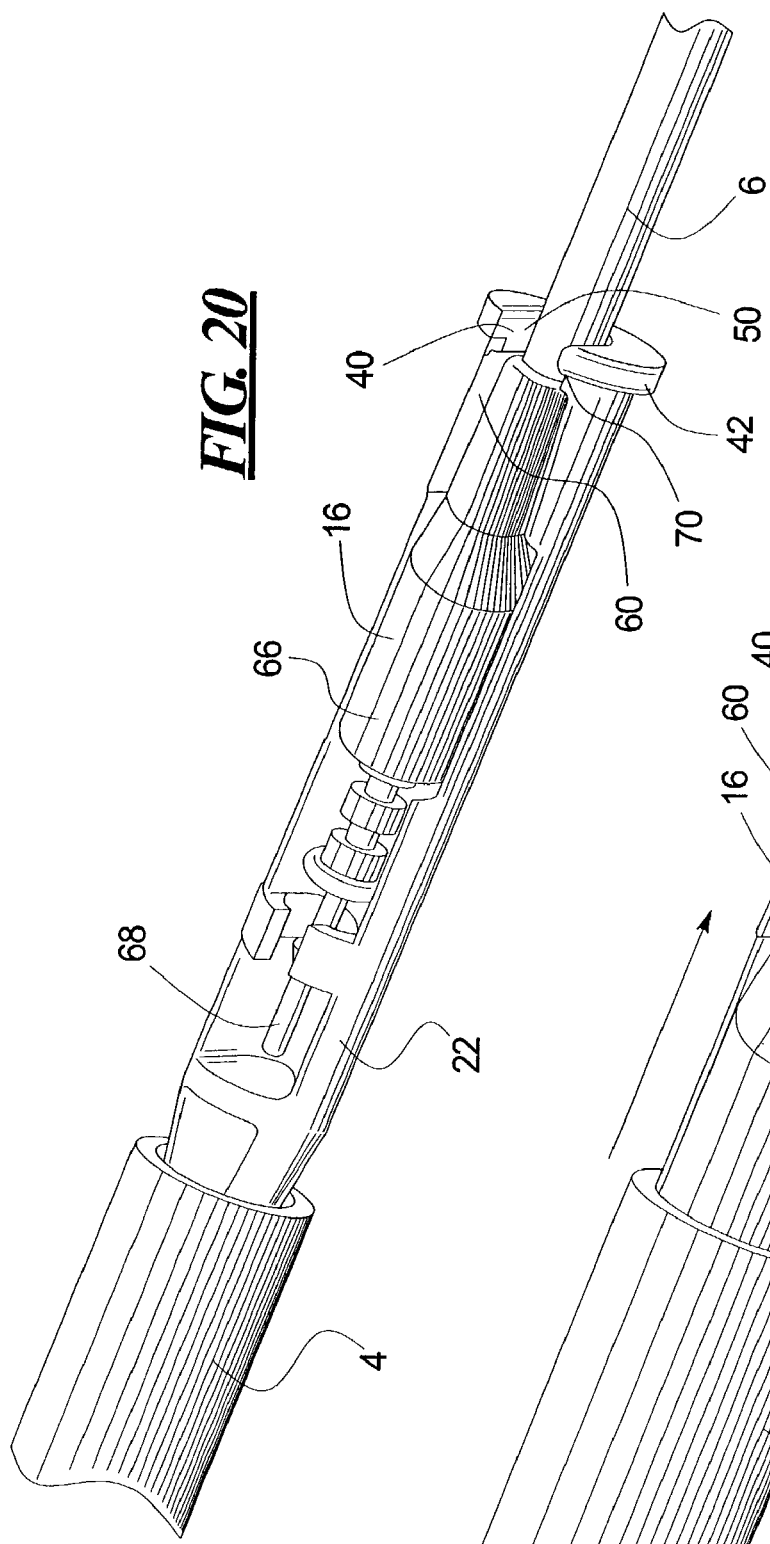
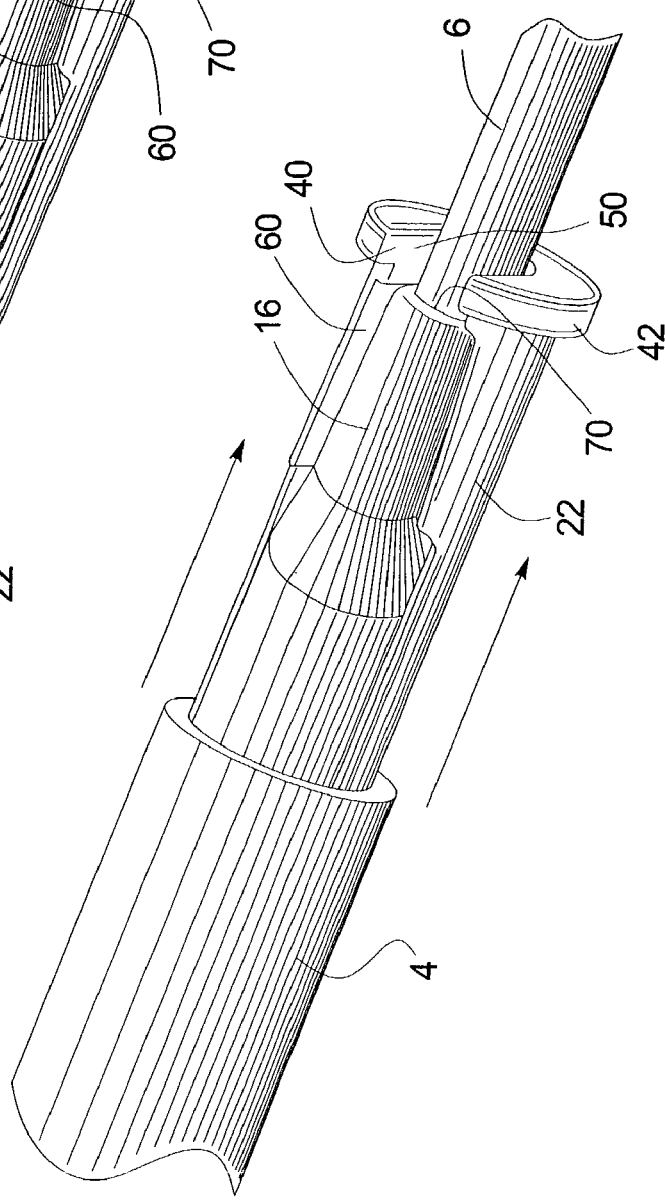

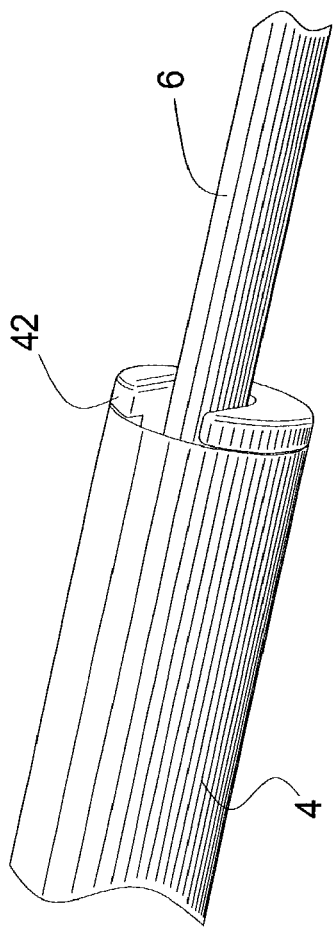
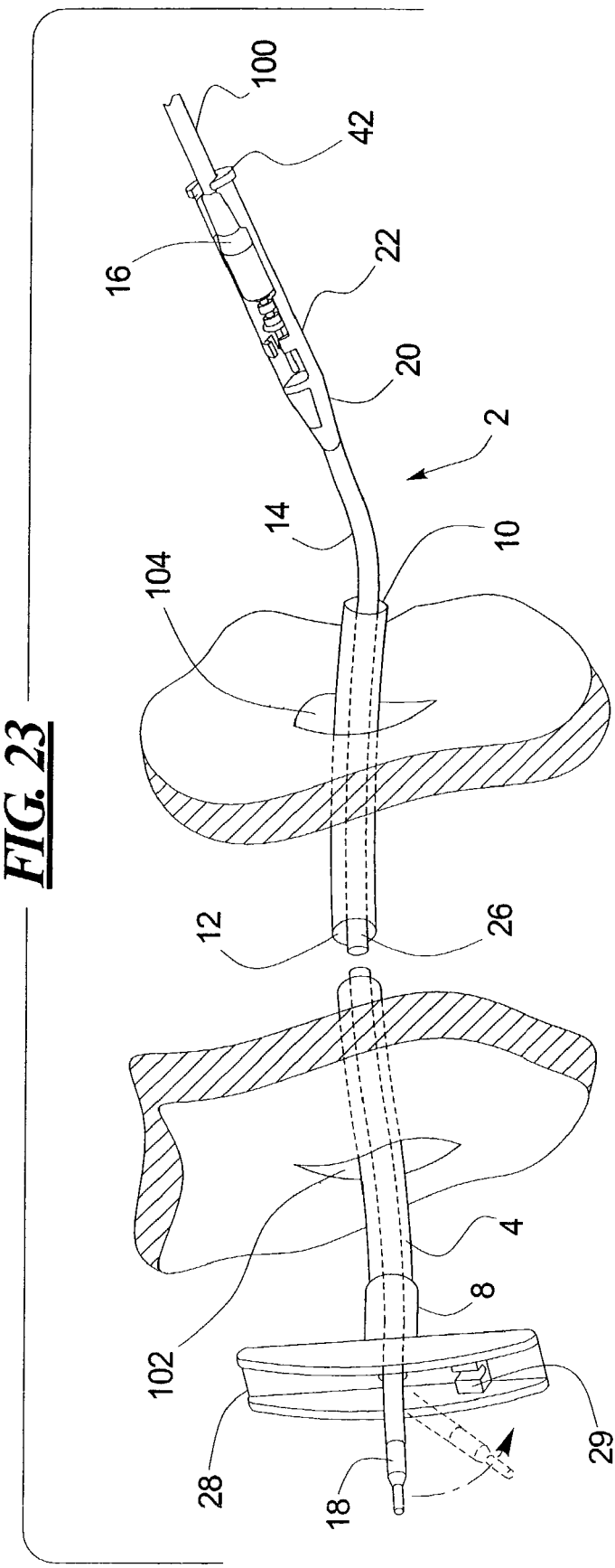

MEDICAL PASSING DEVICE AND METHOD

RELATED APPLICATION

Not applicable.

FIELD OF THE INVENTION

This invention relates to a medical device and method for placing a medical tube or lead within a patient.

BACKGROUND OF THE INVENTION

In numerous medical applications it is necessary to place a medical tube or lead within a patient.

U.S. Pat. No. 4,832,687 teaches a subcutaneous tunneling instrument and method for placing a subcutaneous catheter between two remote incisions in a patient. A subcutaneous tunnel is formed by pushing a rod having an elongated bullet-shaped tip removably threaded upon male threads disposed at the distal end of the rod into one incision and subcutaneously tunneling to and out through the second incision. The bullet-shaped tip is then removed from the distal end of the rod. The open end of a catheter is then slid over the male threads disposed at the distal end of the rod until the catheter abuts the rod. The distal end of the rod is then pulled back into the second incision and through the subcutaneous tunnel and through the first incision, and thereafter removing the open end of the catheter from the male threads at the distal end of the rod. This instrument and method requires appropriately sized male threads for different sized catheters. Further, there is no assurance that the catheter will stay on the male thread as it is being pulled by the rod through the body of a patient.

Another device and method is one comprising an extension passer, an obturator having a sharp end that serves as a tunneling tip, and a carrier. See for example, Medtronic Extension Passer 3555 Accessory Kit (by Medtronic, Inc. of Minneapolis, Minn., the assignee of the present invention). The tunneling tools of this kit are compatible with the Medtronic Neurological Extension Model 7499. In the Medtronic Extension Passer 3555 Accessory Kit, the extension passer is a hollow metal tube or shunt that the obturator can slide through. A handle is attached to the proximal end of the passer and allows the obturator to snap in place for tunneling. The obturator can also be removed and one extension (i.e., a lead) can be manually slid through the passer. The obturator is a narrow plastic cylinder with a sharp distal end that serves as a tunneling tip. The obturator slides through the extension passer and can be snapped in place into the extension passer's handle. The carrier is an attachment like an obturator, but with two distal carrier ports for extension connectors. Either one or two extension connectors can be attached and pulled through the extension passer.

One tunneling procedure using the Medtronic Extension Passer 3555 Accessory Kit comprises tunneling for a single extension without a carrier. In this procedure, with the obturator inserted in the extension passer, a tunnel is made from one incision to second incision or pocket within a patient. The obturator is then removed from the extension passer by unsnapping the end that is attached to the handle and sliding the obturator out from the extension passer at the second incision or pocket. The lead end of the extension is then inserted into the extension passer at the second incision or pocket and slid through the extension passer until it exits at the handle or until fully encompassed by the extension passer. The extension passer is then removed from the tunnel by pulling the handle away from the first incision, thereby leaving the extension in place as desired.

Another tunneling procedure using the Medtronic Extension Passer 3555 Accessory Kit comprises tunneling for a single extension with a carrier. In this procedure, with the obturator inserted in the extension passer, a tunnel is made from one incision to a second incision or pocket within a patient. With the extension passer in place, the obturator is then removed by unsnapping the end that is attached to the handle and sliding the obturator out from the extension passer at the second incision or pocket. Then the carrier is slid into the extension passer at the second incision or pocket until it exits at the handle. Then the proximal end of the carrier is snapped into the handle, leaving a single carrier port exposed at the distal end of the extension passer. The lead end of an extension is then inserted into the carrier port until it snaps into place. The extension passer, with the extension and carrier attached, is then pulled through the tunneled path to where the lead is to be anchored by pulling the handle away from the first incision. The extension passer and carrier are then completely removed from the body of the patient. The lead end of the extension is then removed from the carrier port. This method requires a separate extension passer, an obturator having a tunneling tip, and a carrier.

Another tunneling procedure using the Medtronic Extension Passer 3555 Accessory Kit comprises tunneling for two extensions for a dual-lead system. In this procedure, with the obturator inserted in the extension passer, a tunnel is made from one incision to second incision or pocket within a patient. With the extension passer in place, the obturator is then removed by unsnapping the end that is attached to the handle and sliding the obturator out from the extension passer at the second incision or pocket. Then the carrier is slid into the extension passer at the second incision or pocket until it exits at the handle, leaving both carrier ports exposed at the second incision or pocket. The lead end of an extension is then inserted into the first carrier port until it snaps into place. With the first extension attached to the distal end of the carrier, the proximal end of the carrier is pulled further through the extension passer handle. Then, the proximal end of the carrier is snapped into the handle such that the first carrier port is within the extension passer and the second carrier port remains exposed at the distal end of the extension passer. Then a second extension is placed into the second carrier port. With the extensions attached, the extension passer is then pulled through the tunneled path to where the leads are anchored. The second extension is then removed from the second carrier port. The carrier is then unsnapped from the handle and pushed forward to expose the first carrier port at the distal end. The first extension is then removed from the carrier. This method requires a separate extension passer, an obturator having a tunneling tip, and a carrier.

SUMMARY OF THE INVENTION

The medical device of the present invention comprises a passer having a proximal end and a distal end, the passer defining a channel between the proximal end and the distal end. The medical device of the present invention further comprises an obturator having an elongated body, and a first end and a second end, the second end comprising a cradle. In accordance with the invention, the obturator has a removable probe having a first section that fits within the cradle and a second section having a tunneling tip that is exposed outside of the cradle. The obturator is placed into the passer so that the tunneling tip of the probe is exposed outside of the passer at the distal end of the passer. The cradle has dimensions to receive and hold in place a portion of the medical tube or medical lead after the probe is removed from the cradle.

The present invention includes a method for placing a medical tube or medical lead within a patient, comprising the step of inserting an obturator into a channel of a passer, the passer having a proximal end and a distal end, the obturator having an elongated body, and a first end and a second end. The second end of the obturator comprises a cradle. The obturator has a removable probe having a first section that fits within the cradle, and a second section having a tunneling tip that is exposed outside of the cradle. The method also comprises the step of inserting the obturator into the passer so that the tunneling tip is exposed outside of the passer at the distal end of the passer. The cradle has dimensions to receive and hold in place a portion of the medical tube or medical lead after the probe is removed from the cradle. The method also comprises the steps of making a first incision in the patient, and making a second incision in the patient, the second incision being spaced apart from the first incision. The method also comprises the step of inserting the distal end of the passer into the first incision. The method includes the step of forming a tunnel within a patient using the tunneling tip by moving the distal end the passer from the first incision to the second incision by feeding the passer into the patient at the first incision. The method includes the steps of removing the probe from the cradle of the obturator after the tunneling tip reaches the second incision, and inserting a portion of the medical tube or medical lead into the cradle so that the portion of the medical tube or lead is held within the cradle. The method includes the steps of moving the distal end of the passer back through the tunnel, along with the cradle of the obturator and the portion of the medical tube or medical lead held therein, and removing the portion of the medical tube or medical lead from the cradle of the obturator after the distal end of the passer reaches the first incision, thereby leaving the medical tube or medical lead within the tunnel, and thus within the patient as desired.

The present invention can be used to place within a patient a medical tube, e.g., a catheter that delivers a fluid, such as a medication, to a target site of a patient, or a shunt that allows fluid, such as a bodily fluid, to be removed from a target site of a patient.

The present invention can be used to place within a patient a medical lead, e.g., an electrical conductor, such as an electrical conductor that is used to send electrical current to a target site of a patient and/or an electrical conductor that is used to send electrical current from a sensor to an electrical stimulation device or drug delivery device.

Thus, the present invention provides a device and method that avoids the need of using appropriately sized male threads for different sized catheters and eliminating the risk that the catheter will stay on the male threads as it is being pulled by the rod through the body of a patient as in U.S. Pat. No. 4,832,687. The present invention also avoids the need for a carrier and port separate from the obturator having a tunneling tip as in other prior art devices and methods. Thus, the present invention provides a device having less parts and a more simple and easier method for placing a medical tube or medical lead within a patient. These and other advantages will be recognized by those of skill in the art.

BRIEF DESCRIPTION OF THE DRAWINGS

FIG. 2 illustrates a passer 4 of the medical device of the present invention.

FIG. 3 illustrates an obturator 14 of the medical device of the present invention.

FIG. 4 illustrates an example of the medical device in FIG. 1, further showing the obturator 14 within passer 4.

FIG. 5 illustrates the removal of a probe 24, including the tunneling tip 34, from a cradle 22 after the distal end 10 has been inserted into the first incision 102 and has been moved to the second incision 104.

FIG. 6 illustrates the placement of a portion 16 of a medical tube 6 into cradle 22.

FIG. 7 illustrates the fastening of obturator 14 to a handle 28 of passer 4, and movement of the passer 4 from the second incision towards the first incision.

FIG. 8 illustrates the removal of portion 16 from cradle 22 after the distal end 10 of the passer has reached the first incision.

FIG. 18 illustrates the removal of probe 24 from cradle 22.

FIG. 19 illustrates an assembly 64 comprising a medical tube 6 having a portion 16 before placement of portion 16 into cradle 22.

FIG. 20 illustrates portion 16 after insertion into cradle 22.

FIG. 21 illustrates movement of passer 4 towards flange 42 of cradle 22 after portion 16 has been inserted into cradle 22.

FIG. 22 illustrates the combination of passer 4, flange 42 and medical tube 6, wherein passer 4 and medical tube 6 can be pulled from second incision 104 towards first incision 102, thereby resulting in placement of medical tube 6 within the tunnel within the patient previously made by the tunneling tip 34.

FIG. 23 illustrates an alternative embodiment of the present invention, wherein a medical lead 100 is substituted for medical tube 6. FIG. 23 is identical to FIG. 6, except for a medical lead 100 being substituted for medical tube 6.

DETAILED DESCRIPTION OF THE PREFERRED EMBODIMENTS

Figure 1:
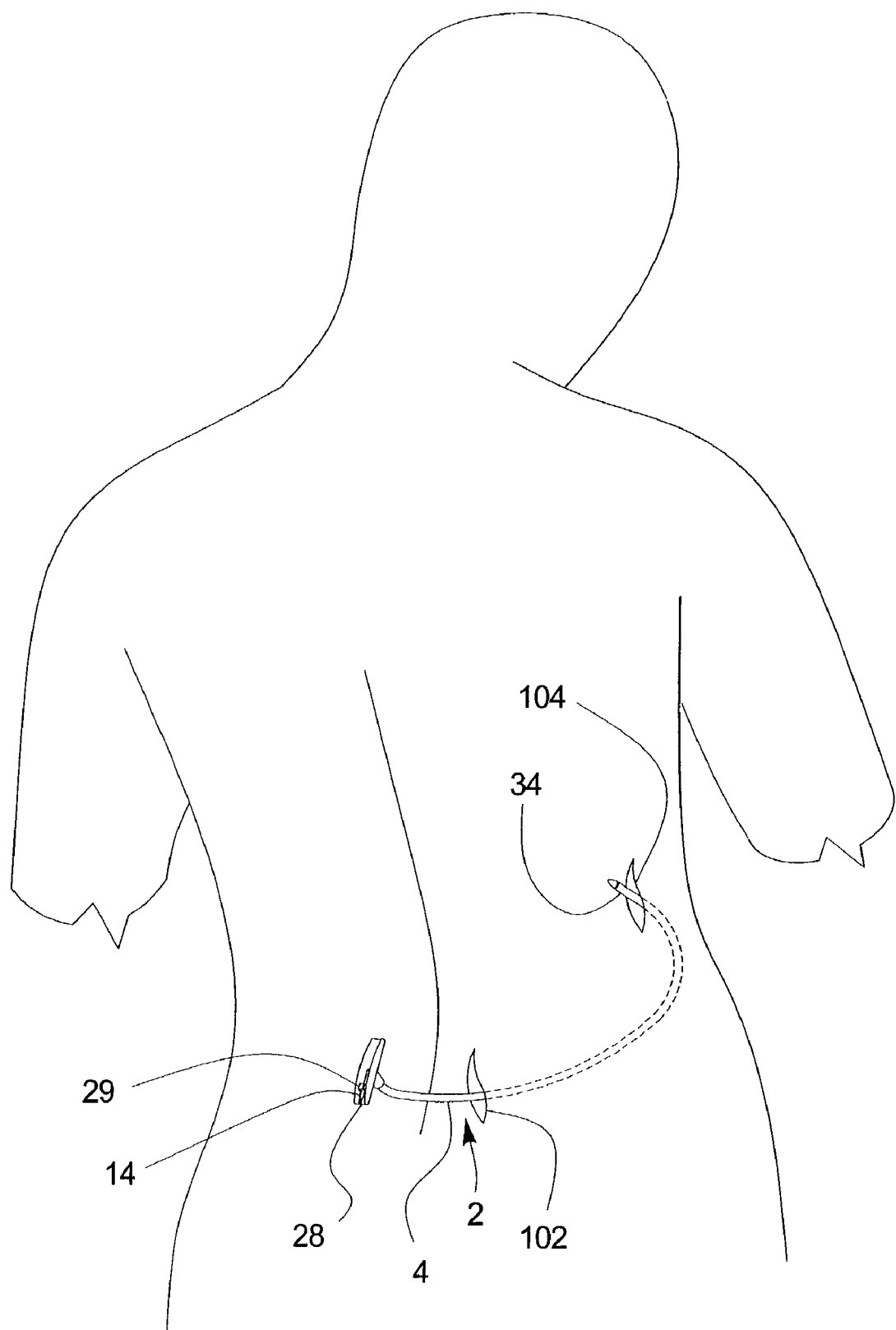
FIG. 1 illustrates an example of a medical device 2 in accordance with the present invention wherein a tunneling tip 34 has been inserted into a patient at a first incision 102 and has been moved to a second incision 104.

As shown in FIGS. 1–8, the present invention comprises a medical device 2 for placing a medical tube 6 within a patient. The medical device of the present invention comprises a passer 4 having a proximal end 8 and a distal end 10, the passer 4 defining a channel 12 between the proximal end 8 and the distal end 10. Medical device 2 further comprises an obturator 14 having an elongated body 26, and a first end 18 and a second end 20, the second end 20 comprising a cradle 22. The obturator 14 has a removable probe 24 having a first section 30 that fits within the cradle 22, and a second section 32 having a tunneling tip 34 that is exposed outside of the cradle 22. The tunneling tip 34 is exposed outside of the passer 4 at the distal end 10 of the passer 4 when the elongated body 26 of the obturator 14 is inserted into the passer 4. The cradle 22 has dimensions to receive and hold in place a portion 16 of the medical tube 6 after the probe 24 is removed from the cradle 22. In a preferred embodiment, tunneling tip 34 comprises a radiopaque material, including but not limited to, a radiopaque plastic. More preferably, tunneling tip 34 comprises a radiopaque plastic such as polypropylene having about 15% by weight barium sulfate.

As shown in FIGS. 1, 4, and 5, a first incision 102 and a second incision 104 are made in the patient at separate locations, and tunneling tip 34 is inserted into incision 102. Tunneling tip 34 is then moved from first incision 102 to second incision 104. This movement can be accomplished by feeding passer 4 into the patient at incision 102. In a preferred embodiment, passer 4 has a handle 28 at proximal end 8, and the first end 18 of obturator 14 can be fastened to handle 28 as may be desired prior to moving tunneling tip 34 from first incision 102 to second incision 104. Obturator 14 can be fastened to handle 28 by using a clip 29. Obturator 14 can have a sleeve 31 for fastening to handle 28. Sleeve 31 can be of any desirable length. As shown in FIG. 3, obturator 14 can comprise a flexible rod 15. Handle 28 can be removable from passer 4, thereby providing flexibility so that a medical tube or medical lead can be inserted into passer 4 at either the proximal end 8 or the distal end 10 of passer 4 as may be desired.

As shown in FIG. 5, after tunneling tip 34 of probe 24 has reached second incision 104, probe 24 is removed from cradle 22. To do this, obturator 14 can be unfastened from handle 28 by unclipping clip 29, thereby allowing second end 20 of obturator 14 to be moved away from distal end 10 of passer 4 and removal of probe 24 from cradle 22.

As shown in FIG. 6, after probe 24 has been removed from cradle 22, a portion 16 of medical tube 6 can be inserted into cradle 22. First end 18 of obturator 14 can then be fastened to handle 28 using clip 29.

As shown in FIG. 7, the combination of passer 4, obturator 14, and medical tube 6 can then be moved from second incision 104 to first incision 102 back through the tunnel previously made by tunneling tip 34.

As shown in FIG. 8, after portion 16 reaches first incision 102, portion 16 can be removed from cradle 22. This can be accomplished by unclipping clip 29 to unfasten first end 18 of obturator 14 from handle 28 and allow second end 20 of obturator 14 to move away from passer 4.

Figure 9:
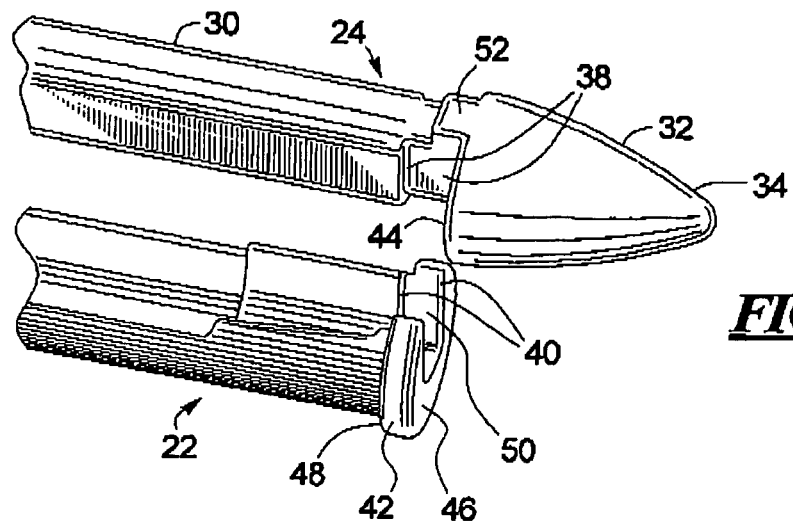
FIG. 9 illustrates mating rib 40 of cradle 22 that corresponds to slot 38 of probe 24.

FIG. 9 illustrates a preferred embodiment of probe 24 and cradle 22. As shown in FIG. 9, cradle 22 comprises a mating rib 40 that corresponds to a slot 38 of probe 24. Thus, when probe 24 is inserted into cradle 22, mating rib 40 slides into slot 38, thereby capturing or grasping probe 24. Cradle 22 also comprises flange 42 having an opening 50. Opening 50 corresponds to a filler section 52 of probe 24. Flange 42 has a first side 46 that abuts a flat surface 44 of probe 24 when the mating rib 40 is placed within slot 38.

Figure 10:
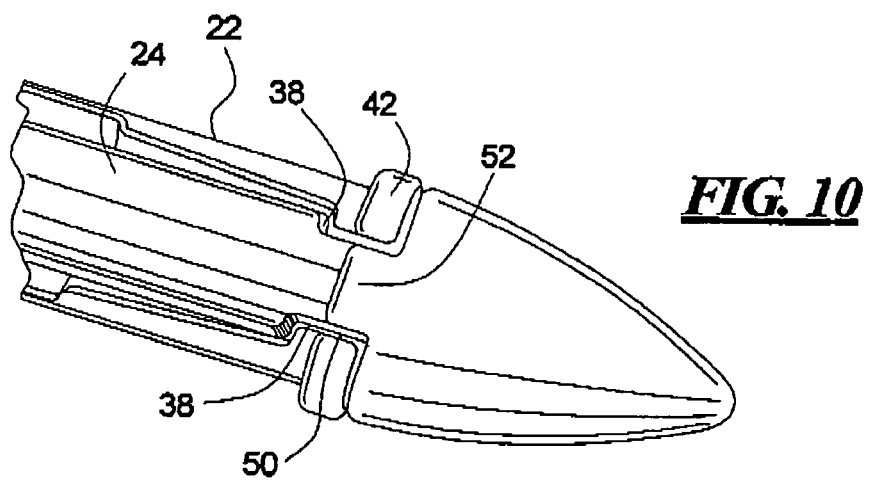
FIG. 10 illustrates mating rib 40 and slot 38 in a captured position.

FIG. 10 illustrates mating rib 40 and slot 38 in the captured position. Preferably, the outside diameter of flange 42 and filler section 52 are substantially equal.

Figure 11:
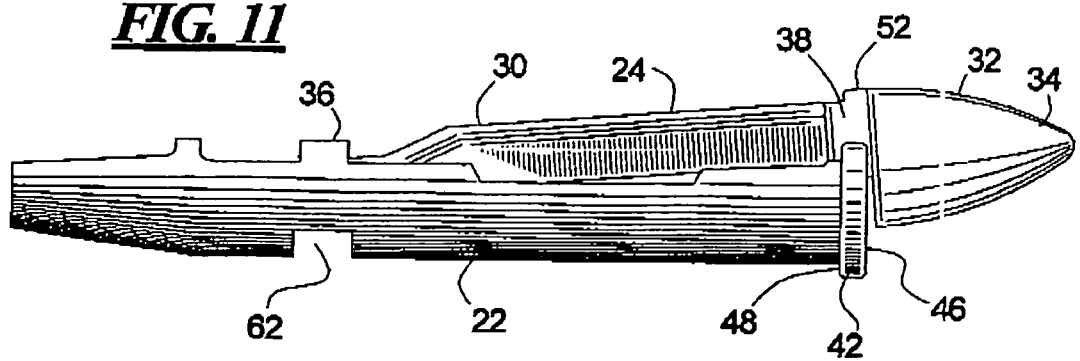
FIG. 11 illustrates a side view of placement of probe 24 into cradle 22.

FIG. 11 illustrates a side view of the placement of probe 24 into cradle 22. The arrows in FIG. 11 show the preferred locations for holding probe 24 within cradle 22. Preferably, at least one member or finger 36 of cradle 22 captures or grasps first section 30 of probe 24. Thus, first section 30 of probe 24 is removably captured by member or finger 36. Thus, when cradle 22 is turned upside down so that probe 24 faces down, probe 24 will not fall out of cradle 22. More preferably, cradle 22 comprises at least two members or fingers 36 to grasp first section 30 of probe 24. Preferably, cradle 22 has a through slot 62 to simplify injection-molding manufacturing of cradle 22 having member(s) or finger(s) 36.

Figure 12:
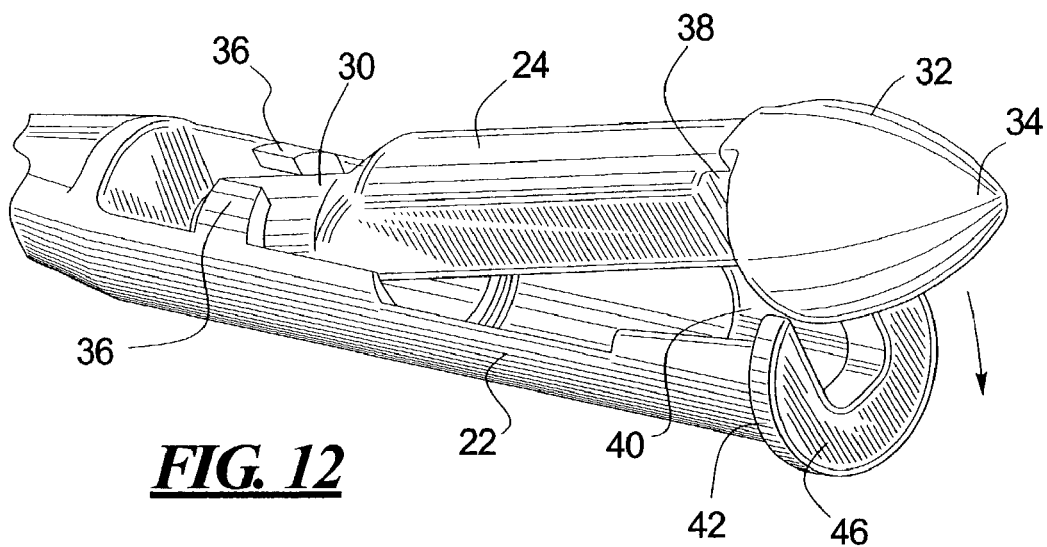
FIG. 12 illustrates a top perspective view of placement of probe 24 into cradle 22.

FIG. 12 illustrates a top perspective view of removal of probe 24 into cradle 22. As shown by the arrows in FIG. 12, members or fingers 36 can be spread apart to allow for easier removal of probe 24 from cradle 22.

Figure 13:
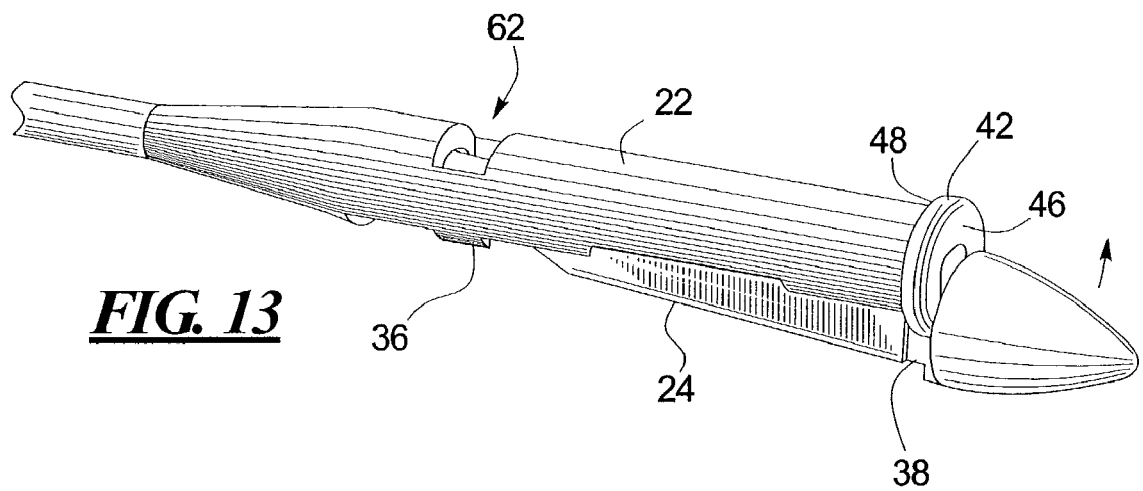
FIG. 13 illustrates a bottom perspective view of placement of probe 24 into cradle 22, including a through slot 62.

FIG. 13 illustrates a bottom perspective view of placement of probe 24 into cradle 22.

Figure 14:
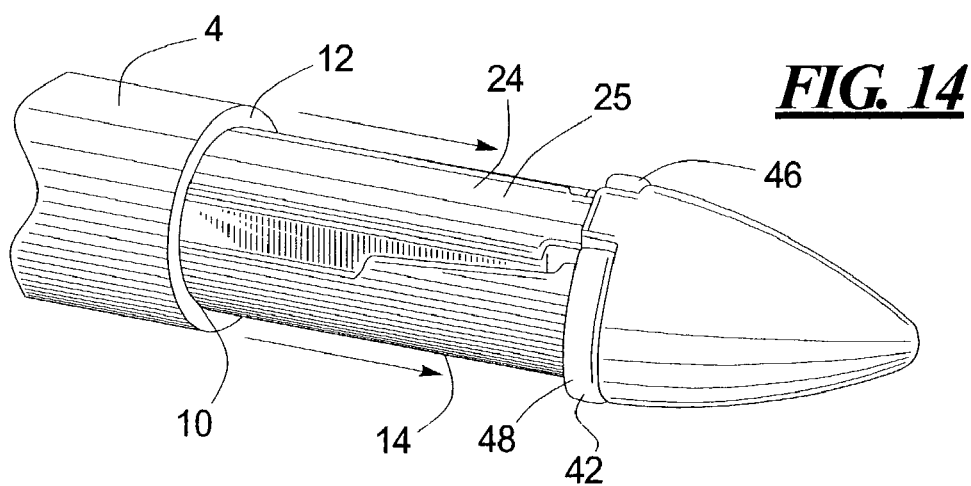
FIG. 14 illustrates a top perspective view of placement of probe 24 into cradle 22, and movement of distal end 10 of passer 4 towards second side 48 of flange 42 of cradle 22.

FIG. 14 illustrates a top perspective view of placement of probe 24 into cradle 22, and movement of distal end 10 of passer 4 towards second side 48 of flange 42 of cradle 22. Preferably, passer 4 comprises a bendable material, such as materials consisting of the group selected from metals and metal alloys, including but not limited to radiopaque materials. Preferably, probe 24 has rounded surfaces 25 that correspond to the inner diameter of passer 4.

Figure 15:
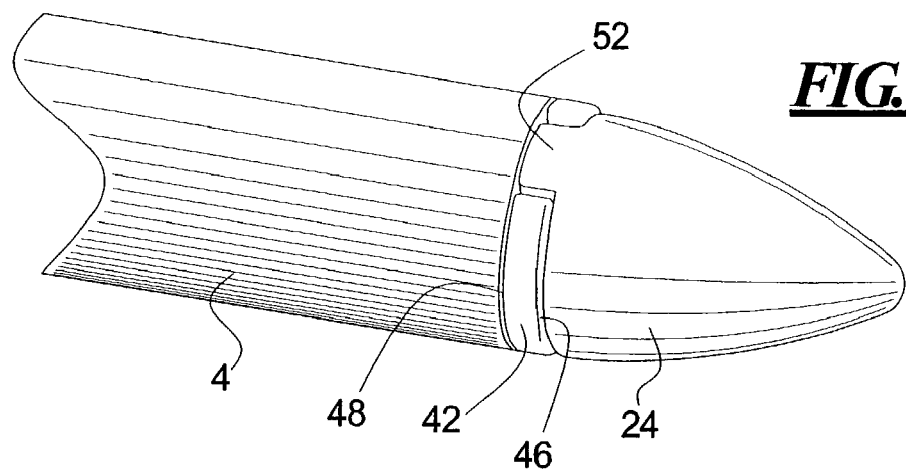
FIG. 15 illustrates the combination of passer 4, flange 42, and filler section 52, all having substantially equal outside diameters.

FIG. 15 illustrates the combination of passer 4, flange 42, and filler section 52, all having substantially equal outside diameters. As shown in FIG. 15, passer 4 abuts second side 48 of flange 42, and also abuts filler section 52 of probe 24.

Figure 16:
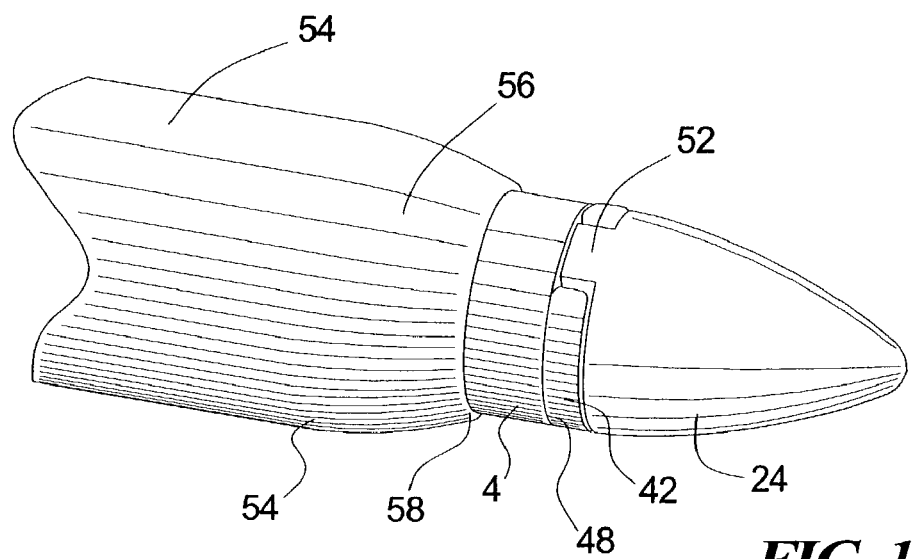
FIG. 16 illustrates the combination shown in FIG. 15, further including a sheath 54.

FIG. 16 illustrates the combination shown in FIG. 15, further including a sheath 54. In a preferred embodiment, the sheath 54 has a tapered end 56. As shown in FIG. 16, in a preferred embodiment, tapered end 56 forms a friction fit 58 with passer 4 at a location separate from where passer 4 abuts second side 48 of flange 42 of cradle 22. Use of sheath 54 provides flexibility so that a medical tube 6 or medical lead 100 can be inserted through either first incision 102 or second incision 104 for placement within a patient after passer 4 and obturator 14 have been removed from sheath 54 at either first incision 102 or second incision 104.

Figure 17:
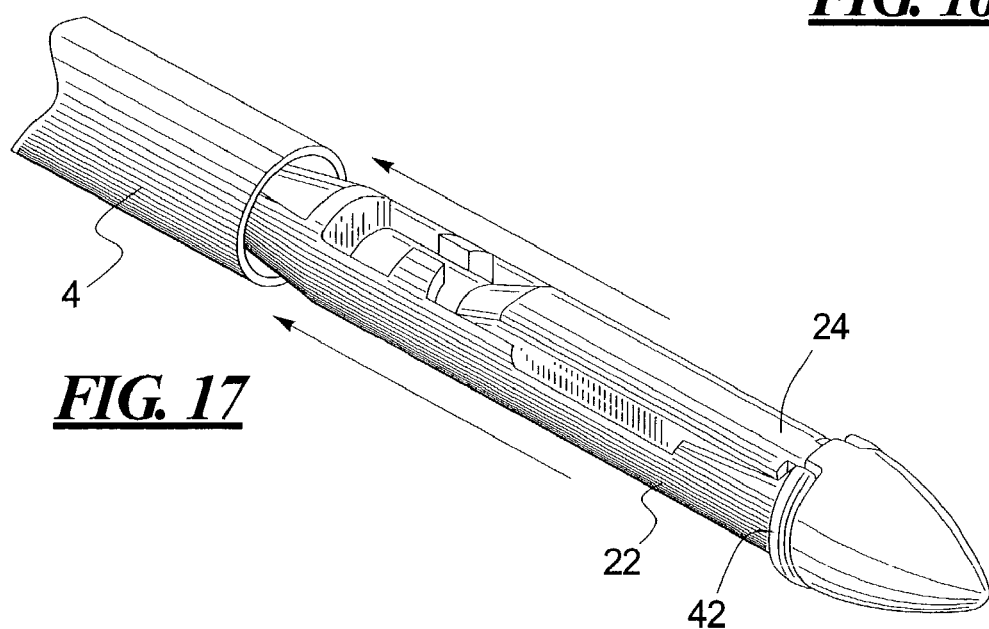
FIG. 17 illustrates the movement of passer 4 away from flange 42 of cradle 22 prior to removal of probe 24 from cradle 22.

FIG. 17 illustrates the movement of passer 4 away from flange 42 of cradle 22 prior to removal of probe 24 from cradle 22.

FIG. 18 illustrates the removal of probe 24 from cradle 22.

FIG. 19 illustrates an assembly 64 comprising a medical tube 6 having a portion 16, and a medical connector 68, before placement of portion 16 into cradle 22. Opening 50 of flange 42 has an appropriate size to receive the medical tube 6. In a preferred embodiment, an edge 70 of portion 16 can be used to abut inner surface 60 of mating rib 40. In a preferred embodiment, portion 16 comprises a medical connector 68, and a strain relief 66. A preferred embodiment of medical connector 68, medical tube 6, and strain relief 66 is described in more detail in U.S. Ser. No. 10/127,853 (assigned to the same assignee as the present invention), and is incorporated herein by reference.

FIG. 20 illustrates portion 16 after insertion into cradle 22. In a preferred embodiment, edge 70 of portion 16 is located on strain relief 66. In a preferred embodiment, strain relief 66 has an outside diameter that corresponds to an inside diameter of cradle 22.

FIG. 21 illustrates movement of passer 4 towards flange 42 of cradle 22 after portion 16 has been inserted into cradle 22.

FIG. 22 illustrates the combination of passer 4, flange 42 and medical tube 6, wherein distal end 10 of passer 4 and medical tube 6 can be pulled from second incision 104 towards first incision 102, thereby resulting in placement of medical tube 6 within the tunnel within the patient previously made by the tunneling tip 34. See also FIGS. 6, 7, and 8.

FIG. 23 illustrates an alternative embodiment of the present invention, wherein a medical lead 100 is substituted for medical tube 6. FIG. 23 is identical to FIG. 6, except for a medical lead 100 being substituted for medical tube 6. Similarly, medical lead 100 can be substituted for medical tube 6 in FIGS. 19 through 22. Thus, the present invention can be used to place either medical tubes or medical leads in a patient.

The present invention includes a method for placing a medical tube 6 or medical lead 100 within a patient, the method comprising: (a) inserting an obturator 14 into a channel 12 of a passer 4, the passer 4 having a proximal end 8 and a distal end 10, the obturator 14 having an elongated body 26, and a first end 18 and a second end 20, the second end 20 comprising a cradle 22, the obturator 14 having a removable probe 24, the removable probe 24 having a first section 30 that fits within the cradle 22 and a second section 32 having a tunneling tip 34 that is exposed outside the cradle 22, (b) making a first incision 102 in the patient, (c) making a second incision 104 in the patient, the second incision 104 being spaced apart from the first incision 102, (d) inserting the distal end 10 of the passer 4 into the first incision 102, (e) forming a tunnel within the patient using a tunneling tip 34 by moving the distal end 10 of the passer 4 from the first incision 102 to the second incision 104 by feeding the passer 4 into the patient at the first incision 102, (f) removing the probe 24 from the cradle 22 of the obturator 14 after the tunneling tip 34 reaches the second incision 104, (g) inserting a portion 16 of the medical tube 6 or medical lead 100 into the cradle 22 so that the portion 16 of the medical tube 6 or medical lead 100 is held within the cradle 22, (h) moving the distal end 10 of the passer 4 back through the tunnel, along with the cradle 22 of the obturator 14 and the portion 16 of the medical tube 6 or medical lead 100 held therein, and (i) removing the portion 16 of the medical tube 6 from the cradle 22 of the obturator 14 after the distal end 10 of the passer 4 reaches the first incision 102, thereby leaving the medical tube 6 or medical lead 100 within the tunnel.

In a preferred embodiment, the method of the present comprises fastening the first end 18 of the obturator 14 to a handle 28 of the passer 4 after step (a) and prior to step (e). In a preferred embodiment, the method further comprises unfastening the first end 18 of the obturator 14 from the handle 28 of the passer 4 after step (e). In a preferred embodiment, the method also comprises fastening the first end 18 of the obturator 14 to the handle 28 of the passer 4 after step (g). In a preferred embodiment, the method also comprises unfastening the first end 18 of the obturator 14 from the handle 28 of the passer 4 after step (h) and prior to step (i).

The preferred embodiments of the invention, and the invention itself, are now described in such full, clear, concise and exact terms to enable a person of ordinary skill in the art to make and use the invention. To particularly point out and distinctly claim the subject matters regarded as invention, the following claims conclude this specification. To the extent variations from the preferred embodiments fall within the limits of the claims, they are considered to be part of the invention, and claimed.

I claim:

1. A medical device for placing a medical tube comprising:
   a passer having a proximal end and a distal end, the passer defining a channel between the proximal end and the distal end,
   an obturator having an elongated body, and a first end and a second end, the second end comprising a cradle, the obturator having a removable probe having a first section that fits within the cradle, and a second section having a tunneling tip that is exposed outside of the cradle,
   the tunneling tip exposed outside of the passer at the distal end of the passer when the elongated body of the obturator is inserted into the passer,
   the cradle having dimensions to receive and hold in place a portion of the medical tube after the probe is removed from the cradle.

2. The medical device of claim 1, further comprising a handle at the proximal end of the passer.

3. The medical device of claim 1, wherein the medical tube is a catheter.

4. The medical device of claim 1, wherein the medical tube is a shunt.

5. The medical device of claim 1, wherein the tunneling tip is bullet-shaped.

6. The medical device of claim 2, wherein the first end of the obturator is removably attached to the handle.

7. The medical device of claim 1, wherein the cradle comprises at least one member that fits over the first section of the probe 8. The medical device of claim 7, wherein the cradle comprises at least two members that fit over the first section of the probe.

9. The medical device of claim 1, wherein the cradle has a mating rib that corresponds to and fits within a slot defined by the probe, the slot located between the first section and the second section of the probe.

10. The medical device of claim 9, wherein the cradle has a flange that abuts a surface of the probe when the mating rib is placed within the slot.

11. The medical device of claim 9, wherein the cradle has a flange having a first side that abuts a flat surface of the probe when the mating rib is placed within the slot, the flange having a second side that abuts the distal end of the passer when the obturator is inserted into the channel of the passer.

12. The medical device of claim 11, wherein the flange defines an opening to receive a filler section of the probe.

13. The medical device of claim 12, wherein the passer, the flange, and the filler section each have substantially the same outside diameter.

14. The medical device of claim 13, further comprising a sheath that covers a majority of the passer, while leaving the tunneling tip exposed.

15. The medical device of claim 14, wherein the sheath has a tapered end that forms a friction fit with the passer.

16. The medical device of claim 11 wherein the mating rib has an inner surface that abuts the portion of the medical tube when the portion is inserted into the cradle.

17. The medical device of claim 2 wherein the handle is removable from the passer.

18. A medical device for placing a medical lead comprising:
a passer having a proximal end and a distal end, the passer defining a channel between the proximal end and the distal end, an obturator having an elongated body, and a first end and a second end, the second end comprising a cradle, the obturator having a removable probe having a first section that fits within the cradle, and a second section having a tunneling tip that is exposed outside of the cradle, the tunneling tip exposed outside of the passer at the distal end of the passer when the elongated body of the obturator is inserted into the passer, the cradle having dimensions to receive and hold in place a portion of the medical lead after the probe is removed from the cradle.

19. The medical device of claim 18, further comprising a handle at the proximal end of the passer.

20. The medical device of claim 18, wherein the tunneling tip is bullet-shaped.

21. The medical device of claim 19, wherein the first end of the obturator is removably attached to the handle.

22. The medical device of claim 18, wherein the cradle comprises at least one member that fits over the first section of the probe.

23. The medical device of claim 22, wherein the cradle comprises at least two members that fit over the first section of the probe.

24. The medical device of claim 18, wherein the cradle has a mating rib that corresponds to and fits within a slot defined by the probe, the slot located between the first section and the second section of the probe.

25. The medical device of claim 24, wherein the cradle has a flange that abuts a surface of the probe when the mating rib is placed within the slot.

26. The medical device of claim 24, wherein the cradle has a flange having a first side that abuts a flat surface of the probe when the mating rib is placed within the slot, the flange having a second side that abuts the distal end of the passer when the obturator is inserted into the channel of the passer.

27. The medical device of claim 26, wherein the flange defines an opening to receive a filler section of the probe.

28. The medical device of claim 27, wherein the passer, the flange, and the filler section each have substantially the same outside diameter.

29. The medical device of claim 28, further comprising a sheath that covers a majority of the passer, while leaving the tunneling tip exposed.

30. The medical device of claim 29, wherein the sheath has a tapered end that forms a friction fit with the passer.

31. The medical device of claim 26 wherein the mating rib has an inner surface that abuts the portion of the medical lead when the portion is inserted into the cradle.

32. The medical device of claim 19 wherein the handle is removable from the passer.

33. A method for placing a medical tube within a patient, the method comprising:
(a) inserting an obturator into a channel of a passer, the passer having a proximal end and a distal end, the obturator having an elongated body, and a first end and a second end, the second end comprising a cradle, the obturator having a removable probe, the removable probe having a first section that fits within the cradle and a second section having a tunneling tip that is exposed outside the cradle,
(b) making a first incision in the patient,
(c) making a second incision in the patient, the second incision being spaced apart from the first incision,
(d) inserting the distal end of the passer into the first incision,
(e) forming a tunnel within the patient using a tunneling tip by moving the distal end of the passer from the first incision to the second incision by feeding the passer into the patient at the first incision,
(f) removing the probe from the cradle of the obturator after the tunneling tip reaches the second incision,
(g) inserting a portion of the medical tube into the cradle so that the portion of the medical tube is held within the cradle,
(h) moving the distal end of the passer back through the tunnel, along with the cradle of the obturator and the portion of the medical tube held therein, and
(i) removing the portion of the medical tube from the cradle of the obturator after the distal end of the passer reaches the first incision, thereby leaving the medical tube within the tunnel.

34. The method of claim 33, comprising fastening the first end of the obturator to a handle of the passer after step (a) and prior to step (e).

35. The method of claim 34, comprising unfastening the first end of the obturator from the handle of the passer after step (e).

36. The method of claim 35, comprising fastening the first end of the obturator to the handle of the passer after step (g).

37. The method of claim 36, comprising unfastening the first end of the obturator from the handle of the passer after step (h) and prior to step (i).

38. A method for placing a medical lead within a patient, the method comprising:
(a) inserting an obturator into a channel of a passer, the passer having a proximal end and a distal end, the obturator having an elongated body, and a first end and a second end, the second end comprising a cradle, the obturator having a removable probe, the removable probe having a first section that fits within the cradle and a second section having a tunneling tip that is exposed outside the cradle,
(b) making a first incision in the patient,
(c) making a second incision in the patient, the second incision being spaced apart from the first incision,
(d) inserting the distal end of the passer into the first incision,
(e) forming a tunnel within the patient using a tunneling tip by moving the distal end of the passer from the first incision to the second incision by feeding the passer into the patient at the first incision,
(f) removing the probe from the cradle of the obturator after the tunneling tip reaches the second incision,
(g) inserting a portion of the medical lead into the cradle so that the portion of the medical lead is held within the cradle,
(h) moving the distal end of the passer back through the tunnel, along with the cradle of the obturator and the, portion of the medical lead held therein, and
(i) removing the portion of the medical lead from the cradle of the obturator after the distal end of the passer reaches the first incision, thereby leaving the medical lead within the tunnel.

39. The method of claim 38, comprising fastening the first end of the obturator to a handle of the passer after step (a) and prior to step (e).

40. The method of claim 39, comprising unfastening the first end of the obturator from the handle of the passer after step (e).

41. The method of claim 40, comprising fastening the first end of the obturator to the handle of the passer after step (g).

42. The method of claim 41, comprising unfastening the first end of the obturator from the handle of the passer after step (h) and prior to step (i).

* * * * *